United States Patent [19]

Aramaki et al.

[11] Patent Number: 5,265,850
[45] Date of Patent: Nov. 30, 1993

[54] REFRACTORY FOR GAS BLOWING FOR MOLTEN METAL REFINING VESSEL

[75] Inventors: Keizo Aramaki; Tomohiro Okumura, both of Tajimi, Japan

[73] Assignee: Tokyo Yogyo Kabushiki Kaisha, Tokyo, Japan

[21] Appl. No.: 910,626

[22] Filed: Jul. 8, 1992

[51] Int. Cl.$^5$ .............................................. B22D 41/58
[52] U.S. Cl. ..................... 266/220; 266/217
[58] Field of Search ................ 266/217, 220, 265, 270

[56] References Cited

U.S. PATENT DOCUMENTS

| | | | |
|---|---|---|---|
| 3,053,525 | 9/1962 | Leroy et al. | 266/220 |
| 3,330,645 | 7/1967 | Moustier et al. | 266/220 |
| 4,266,970 | 5/1981 | Iwaoka et al. | 75/59 |
| 4,539,043 | 9/1985 | Miyawaki et al. | 266/270 |
| 4,647,020 | 3/1987 | Liesch et al. | 266/270 |
| 5,104,097 | 4/1992 | Naujokat et al. | 266/217 |

OTHER PUBLICATIONS

Tekko Binran (Iron and Steel Handbook) 3rd Ed., vol. 11, Ironmaking and Steelmaking, Sep. 20, 1980, p. 796.

*Primary Examiner*—Scott Kastler
*Attorney, Agent, or Firm*—Frishauf, Holtz, Goodman & Woodward

[57] ABSTRACT

A refractory for gas blowing to be attached to an opening of a molten metal refining vessel includes a gas permeable portion comprising an alumina refractory, the gas permeable portion having a plurality of gas blowing apertures running therethrough in the axial direction thereof, and a collar portion comprising an alumina refractory, formed integrally with the gas permeable portion so as to surround the gas permeable portion. The alumina refractory for both the gas permeable portion and the collar portion contains at least 88 wt. % alumina and is substantially non-porous with a porosity of up to 20%.

5 Claims, 1 Drawing Sheet

REFRACTORY FOR GAS BLOWING FOR MOLTEN METAL REFINING VESSEL

REFERENCE TO PATENTS, APPLICATIONS AND PUBLICATIONS PERTINENT TO THE INVENTION

The following prior art document pertinent to the present invention:

TEKKO BINRAN (Iron and Steel Handbook), third ed., Vol. 11, "Ironmaking and Steelmaking," published Sep. 20, 1980, page 796.

The contents of the prior art disclosed in the above-mentioned prior art document will be discussed hereafter under the heading of the "BACKGROUND OF THE INVENTION."

BACKGROUND OF THE INVENTION

The present invention relates to a refractory for gas blowing to be attached to an opening of a molten metal refining vessel.

RELATED ART STATEMENT

In order to apply a vacuum decarburization, an adjustment of chemical composition, degassing or other refining treatment to a molten metal received in a metal refining vessel, it is the usual practice to blow a gas such as an argon gas and a nitrogen gas into the molten metal in the refining vessel under a vacuum or under an atmospheric pressure.

As disclosed in the TEKKO BINRAN (Iron and Steel Handbook) third ed., Vol. 11, "Ironmaking and Steelmaking," published Sep. 20, 1980, page 796, it is conventionally common to provide a bottom wall of a molten metal refining vessel with an opening running therethrough. The opening is provided with a collar portion comprising a refractory, and a porous plug comprising a porous refractory, which has a shape matching with the collar portion, is releasably attached to the collar portion from the outside of the bottom wall. FIG. 1 is a schematic vertical sectional view illustrating a conventional refractory for gas blowing used as a porous plug, attached to a collar portion of an opening in the bottom wall of a molten metal refining vessel. In FIG. 1, 1 is a porous plug comprising a porous refractory, 2 is a collar portion comprising a refractory, of an opening provided in the bottom wall of a molten metal refining vessel, 3 is a mortar joint for jointing the porous plug 1 to the collar portion 2, and 11 is a gas supply pipe. FIG. 2 is a schematic vertical sectional view illustrating another conventional refractory for gas blowing used as a porous plug, attached to a collar portion of an opening in the bottom wall of a molten metal refining vessel. In FIG. 2, 1 is a porous plug comprising a porous refractory, 2 is a collar portion comprising a refractory, of an opening provided in the bottom wall of a molten metal refining vessel, 4 is a porous sleeve comprising a porous refractory, 3 and 5 are mortar joints for jointing the porous plug 1 to the porous sleeve 4, and the porous sleeve 4 to the collar portion 2, respectively, and 11 is a gas supply pipe (hereinafter referred to as the "prior art").

When a refining gas having a pressure higher than a static pressure of a molten metal received in a refining vessel is blown from below through the gas supply pipe 11 and the porous plug 1 into the molten metal in the refining vessel, the molten metal in the refining vessel is stirred by means of the refining gas blown through the porous plug 1 and thus refined.

The prior art has however the following problems.

A porous plug 1 comprising a porous refractory, having a short service life, must be frequently replaced. Because the porous plug 1 comprising the porous refractory tends to be easily damaged, furthermore, the operation of attaching the porous plug 1 to a collar portion 2 of an opening of a molten metal refining vessel incidental to the replacement, must be conducted carefully. This leads to a long replacement time of the porous plug 1 and a lower operating rate of the molten metal refining vessel. In addition, during the refining of molten metal or upon the pickling of the porous plug 1, the mortar joint 3 which joints the porous plug 1 to the collar portion 2 comprising a refractory is eroded, thus causing the porous plug 1 to fall off from the refining vessel. This further reduces the service life of the porous plug 1 or makes it more difficult to accomplish a stable refining.

Under such circumstances, there is a strong demand for the development of a refractory for gas blowing to be attached to an opening of a molten metal refining vessel, which permits a stable blowing of a gas for refining a molten metal received in the refining vessel, prevents penetration of the molten metal, and has a long service life, but such a refractory has not as yet been proposed.

SUMMARY OF THE INVENTION

An object of the present invention is therefore to provide a refractory for gas blowing to be attached to an opening of a molten metal refining vessel, which permits a stable blowing of a gas for refining a molten metal received in the refining vessel, prevents penetration of the molten metal, and has a long service life.

In accordance with one of the features of the present invention, there is provided a refractory for gas blowing to be attached to an opening of a molten metal refining vessel, which comprises:

a gas permeable portion comprising an alumina refractory, said gas permeable portion having a plurality of gas blowing apertures running therethrough in the axial direction thereof;

a collar portion comprising an alumina refractory, formed integrally with said gas permeable portion so as to surround said gas permeable portion; and said alumina refractory containing at least 88 wt. % alumina and being substantially non-porous with a porosity of up to 20%.

DETAILED DESCRIPTION OF PREFERRED EMBODIMENTS

From the above-mentioned point of view, extensive studies were carried out to develop a refractory for gas blowing to be attached to an opening of a molten metal refining vessel, which permits a stable blowing of a gas for refining a molten metal received in the refining vessel, prevents penetration of the molten metal, and has a long service life.

As a result, the following findings were obtained: by using, in place of the conventional porous plug, a refractory which comprises a gas permeable portion comprising a non-porous and dense refractory excellent in corrosion resistance, which gas permeable portion has a plurality of gas blowing apertures, on the one hand, and a collar portion comprising a non-porous and dense refractory excellent in corrosion resistance, formed integrally with the gas permeable portion so as to surround the gas permeable portion, on the other hand, it is possible to extend the service life of a molten metal refining vessel and improve the operating rate of the refining vessel. By forming the collar portion integrally with the gas permeable portion as described above, it is possible to eliminate the mortar joint as used in the above-mentioned prior art for jointing the porous plug to the collar portion, which is eroded preferentially to the other portions during the refining of molten metal or upon the pickling of the porous plug, permit a stable blowing of the refining gas, and further extend the service life of the refining vessel.

The present invention was made on the basis of the above-mentioned findings. The refractory for gas blowing of the present invention to be attached to a opening of a molten metal refining vessel, comprises:

a gas permeable portion comprising an alumina refractory, said gas permeable portion having a plurality of gas blowing apertures running therethrough in the axial direction thereof;

a collar portion comprising an alumina refractory, formed integrally with said gas permeable portion so as to surround said gas permeable portion; and said alumina refractory containing at least 88 wt. % alumina and being non-porous with a porosity of up to 20%.

The terms non-porous and substantially non-porous are used herein to describe a refractory with a porosity of up to 20%.

Now, embodiments of the present invention are described below with reference to the drawings.

Figure 3:
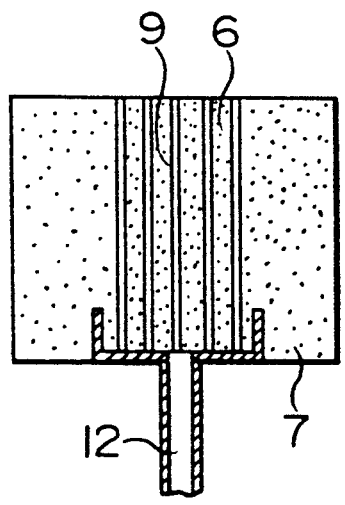
FIG. 3 is a schematic vertical sectional view illustrating a first embodiment of a refractory for gas blowing of the present invention, to be attached to an opening of a molten metal refining vessel.

FIG. 3 is a schematic vertical sectional view illustrating a first embodiment of a refractory for gas blowing of the present invention, to be attached to an opening of a molten metal refining vessel. In FIG. 3, 6 is a gas permeable portion having a columnar shape, 7 is a collar portion formed so as to surround the gas permeable portion 6, and 12 is a gas supply pipe. In the refractory for gas blowing of the first embodiment, the gas permeable portion 6 and the collar portion 7 are integrally formed of refractories having the same chemical composition. In the gas permeable portion 6, a plurality of gas blowing apertures 9 in the form of slits, which run through the gas permeable portion 6 in the axial direction thereof, are formed to blow a refining gas. Each of the plurality of gas blowing apertures 9 has a size sufficient to prevent, after the stoppage of gas blowing, the molten metal received in the refining vessel from flowing out of the refining vessel through the gas blowing apertures 9. The refining gas blown through the gas supply pipe 12 for the refractory for gas blowing attached to the opening in the bottom wall of the molten metal refining vessel, is blown through the plurality of gas blowing apertures 9 into molten metal received in the refining vessel.

Figure 4:
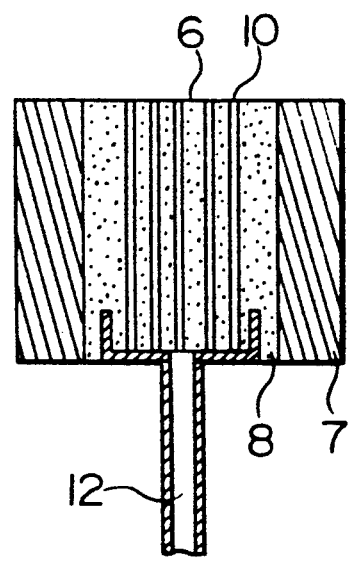
FIG. 4 is a schematic vertical sectional view illustrating a second embodiment of a refractory for gas blowing of the present invention, to be attached to an opening of a molten metal refining vessel.

FIG. 4 is a schematic vertical sectional view illustrating a second embodiment of a refractory for gas blowing of the present invention, to be attached to an opening of a molten metal refining vessel. In FIG. 4, 6 is a gas permeable portion having a columnar shape, 7 and 8 are collar portions formed so as to surround the gas permeable portion 6, and 12 is a gas supply pipe. In the refractory for gas blowing of the second embodiment, the gas permeable portion 6 and a part 8 of the collar portion are formed of refractories having the same chemical composition, and the remaining part 7 of the collar portion is formed of a refractory having a chemical composition different from that of the refractories for the gas permeable portion 6 and that portion 8 of the collar portion. Furthermore, the gas permeable portion 6 and the collar portions 7 and 8 are formed integrally with each other. In the gas permeable portion 6, a plurality of gas blowing apertures 10 in the form of circular apertures, which run through the gas permeable portion 6 in the axial direction thereof, are formed to blow a refining gas. Each of the plurality of gas blowing apertures 10 has a size sufficient to prevent, after the stoppage of gas blowing, the molten metal received in the refining vessel from flowing out of the refining vessel through the gas blowing apertures 10. The refining gas blown through the gas supply pipe 12 for the refractory for gas blowing attached to the opening in the bottom wall of the molten metal refining vessel, is blown through the plurality of gas blowing apertures 10 into the molten metal received in the refining vessel.

Depending upon the purpose of use, as described above, the gas permeable portion and the collar portion may be formed of refractories having the same chemical composition, the gas permeable portion and the collar portion may be formed of refractories having different chemical compositions; the gas permeable portion and a part of the collar portion may be formed of refractories having the same chemical composition, or that part of the collar portion and the remaining part of the collar portion may be formed of refractories having different chemical compositions.

The refractories of the gas permeable portion and the collar portion should contain at least 88 wt. % alumina ($Al_2O_3$) to ensure a high corrosion resistance, and should be non-porous with a porosity of up to 20% to exhibit a high density.

Each of the plurality of gas blowing apertures 9 in the form of slits, which run through the gas permeable portion 6 in the axial direction thereof, should have a width of up to 0.25 mm so as to prevent, after the stoppage of gas blowing, the molten metal received in the refining vessel from flowing out of the refining vessel through the gas blowing apertures 9. Each of the plurality of gas blowing apertures 10 in the form of circular apertures, which run through the gas permeable portion 6 in the axial direction thereof, should have a diameter of up to 0.6 mm so as to prevent, after the stoppage of gas blowing, the molten metal received in the refining vessel from flowing out of the refining vessel through the gas blowing apertures 10.

Now, the refractory for gas blowing of the present invention is described further in detail by means of examples while comparing with examples for comparison.

EXAMPLE 1

A sample of the refractory for gas blowing of the present invention as shown in FIG. 3 (hereinafter referred to as the "sample of the invention") No. 1 was prepared, which comprised a gas permeable portion 6 having a columnar shape with a diameter of 105 mm and a height of 360 mm, and a collar portion 7 formed integrally with the gas permeable portion 6 so as to surround the gas permeable portion 6, and had a shape of rectangular parallelepiped with a length of 400 mm, a width of 400 mm and a height of 360 mm.

In the gas permeable portion 6, 32 gas blowing apertures 9 in the form of slits, which ran through the gas permeable portion 6 in the axial direction thereof, were provided to blow a refining gas. Each of the gas blowing apertures 9 had a rectangular cross sectional area of 0.25 mm × 10 mm. The gas permeable portion 6 and the collar portion 7 were integrally formed of refractories having the same chemical composition containing 88 wt. % alumina and having a porosity of 10%, as shown in Table 1. The other properties of the sample of the invention No. 1 were as shown in Table 1. The column in Table 1 heading "Gas flow rate" means a flow rate per minute of a refining gas which has passed through the sample of the invention No. 1, when there is a pressure difference of 2 Kg/cm$^2$ between the entry of the gas supply pipe 12 and the exit of the gas blowing aperture 9.

The sample of the invention No. 1 prepared as described above was attached to the opening in the bottom wall of a 150-ton ladle, and the ladle refining of molten steel was conducted by blowing an argon gas from the gas supply pipe 12 through the gas blowing apertures 9 in the gas permeable portion 6 into molten steel received in the ladle. As a result, according to the sample of the invention No. 1, the 150-ton ladle showed a service life of from 34 to 37 heats, or 35.2 consecutive heats on the average, without requiring the replacement of the sample of the invention No. 1.

Figure 1:
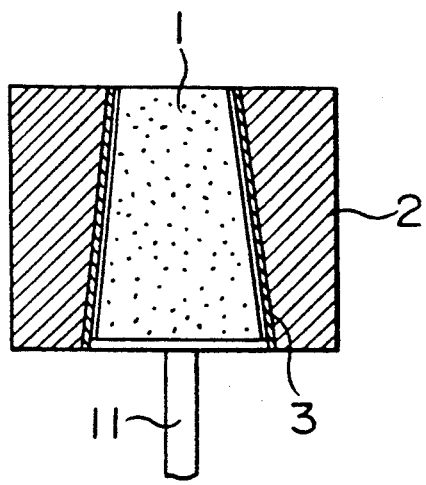
FIG. 1 is a schematic vertical sectional view illustrating a conventional refractory for gas blowing used as a porous plug, attached to a collar portion of an opening in the bottom wall of a molten metal refining vessel.
Figure 2:
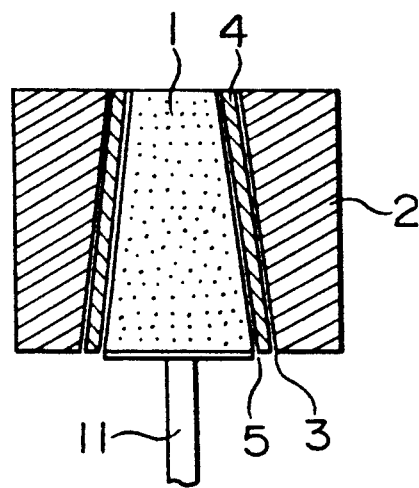
FIG. 2 is a schematic vertical sectional view illustrating another conventional refractory for gas blowing used as a porous plug, attached to a collar portion of an opening in the bottom wall of a molten metal refining vessel.

For comparison purposes, a sample of the conventional porous plug 1 as shown in FIG. 1 (hereinafter referred to as the "sample for comparison") No. 1 was prepared. The sample for comparison No. 1 was attached through the mortar joint 3 to the collar portion 2 of the opening in the bottom wall of a 150-ton ladle, and the ladle refining of molten steel was conducted by blowing an argon gas from the gas supply pipe 11 through the sample for comparison No. 1 into molten steel received in the ladle. As a result, according to the sample for comparison No. 1, the 150-ton ladle showed the service life of from 17 to 30 heats, or 23.5 consecutive heats on the average, while requiring 3 to 5 replacements of the sample for comparison No. 1.

EXAMPLE 2

A sample of the refractory for gas blowing of the present invention as shown in FIG. 4 (hereinafter referred to as the "sample of the invention") No. 2 was prepared, which comprised a gas permeable portion 6 having a columnar shape with a diameter of 83 mm and a height of 250 mm, and collar portions 7 and 8 formed so as to surround the gas permeable portion 6, and had a shape of rectangular parallelepiped with a length of 400 mm, a width of 400 mm and a height of 250 mm.

In the gas permeable portion 6, 48 gas blowing apertures 10 in the form of circular apertures, which ran through the gas permeable portion 6 in the axial direction thereof, were provided to blow a refining gas. Each of the gas blowing apertures 10 had a circular cross sectional area of a diameter of 0.6 mm. The gas permeable portion 6 and a part 8 of the collar portion within a range of a radius of 60 mm from the center of the gas permeable portion 6 were formed of refractories having the same chemical composition containing 95 wt. % alumina and having a porosity of 8.5%, as shown in Table 1, and the remaining part 7 of the collar portion was formed of another refractory having a different chemical composition containing 88 wt. % alumina and having a porosity of 10.0%. The gas permeable portion 6 and the collar portions 7 and 8 were formed integrally with each other. The other properties of the sample of the invention No. 2 were as shown in Table 1.

The sample of the invention No. 2 prepared as described above was attached to the opening in the bottom wall of an 80-ton ladle, and the ladle refining of molten steel was conducted by blowing an argon gas from the gas supply pipe 12 through the gas blowing apertures 10 in the gas permeable portion 6 into molten steel received in the ladle. As a result, according to the sample of the invention No. 2, the 80-ton ladle showed a service life of from 22 to 25 heats, or 23.9 consecutive heats on the average, without requiring the replacement of the sample of the invention No. 2.

For comparison purposes, a sample of the conventional porous plug 1 as shown in FIG. 1 (hereinafter referred to as the "sample for comparison") No. 2 was prepared. The sample for comparison No. 2 was attached through the mortar joint 3 to the collar portion 2 of the opening in the bottom wall of an 80-ton ladle,

TABLE 1

| | | Samples of the invention No. 1 | | Sample of the invention No. 2 | | Samples for comparison Nos. 1 and 2 | |
|---|---|---|---|---|---|---|---|
| | | | | Gas permeable | | | |
| | | Gas permeable portion | Collar portion | portion and a part of collar portion | Remaining part of collar portion | Porous plug | Collar portion |
| Chemical composition | Al$_2$O$_3$ | 88 | 88 | 95 | 88 | 88.4 | 88 |
| | SiO$_2$ | 10 | 10 | 4 | 10 | 6.1 | 10 |
| | Cr$_2$O$_3$ | — | — | — | — | 3.0 | — |
| | Others | 2 | 2 | 1 | 2 | 2.5 | 2 |
| Porosity | | 10 | 10 | 10 | 10 | 22.1 | 10 |
| Blue density | | 3.1 | 3.1 | 3.2 | 3.1 | 2.92 | 3.1 |
| Compressive strength | | 400 | 400 | 450 | 400 | 450 | 400 |
| Gas flow rate (Nl/minute) | | 450 | — | 250 | — | 320 | — | and the ladle refining of molten steel was conducted by blowing an argon gas from the gas supply pipe 11 through the sample for comparison No. 2 into molten steel received in the ladle. As a result, according to the sample for comparison No. 2, the 80-ton ladle showed the service life of from 9 to 14 heats, or 13.3 consecutive heats on the average, while requiring 2 to 4 replacements of the sample for comparison No. 2.

As is clear from the above description, the samples of the invention Nos. 1 and 2 have a remarkably longer service life and a large number of consecutive heats, and permits use of a refractory having an excellent corrosion resistance, as compared with the samples for comparison Nos. 1 and 2. Furthermore, contrary to the above-mentioned prior art, almost no erosion is caused during the refining of molten metal and upon the pickling, and replacement of the porous plug is not required, thus permitting improvement of the operating rate of the molten metal refining vessel.

According to the refractory for gas blowing of the present invention, as described above in detail, it is possible to stably blow a gas for refining a molten metal received in a refining vessel for a long period of time, and prevent penetration of the molten metal, thus providing many industrially useful effects.

What is claimed is:

1. A refractory for gas blowing to be attached to an opening of a molten metal refining vessel, which comprises:

a gas permeable portion comprising an alumina non-porous refractory containing at least 88 wt. % alumina, said alumina refractory of said gas permeable portion being substantially non-porous and having a porosity of up to 20%, and said gas permeable portion having a plurality of gas blowing apertures running therethrough in an axial direction thereof; and a collar portion comprising an alumina refractory containing at least 88 wt. % alumina, said collar portion being formed integrally with said gas permeable portion so as to surround said gas permeable portion, and said alumina refractory of said collar portion being substantially non-porous and having a porosity of up to 20%.

2. A refractory for gas blowing as claimed in claim 1, wherein:

each of said plurality of gas blowing apertures comprises a slit, each of said slits having substantially a rectangular cross-sectional shape, and a shorter side of each slit having a length of up to 0.2 mm.

3. A refractory for gas blowing as claimed in claim 1, wherein:

each of said plurality of gas blowing apertures comprises a circular aperture, and each of said circular apertures has a cross-sectional diameter of up to 0.6 mm.

4. A refractory for gas blowing as claimed in claim 2 or 3, wherein:

said gas permeable portion and said collar portion are formed of alumina refractories having the same chemical composition.

5. A refractory for gas blowing as claimed in claim 2 or 3, wherein:

said gas permeable portion and said collar portion are formed of alumina refractories having a different chemical composition from each other.

* * * * *